United States Patent [19]

Burns et al.

[11] Patent Number: 4,826,775
[45] Date of Patent: May 2, 1989

[54] DILUTION APPARATUS AND METHOD

[75] Inventors: Donald A. Burns, Putnam Valley; Anthony F. Buccafuri, Suffern, both of N.Y.

[73] Assignee: Alfa-Laval AB, Sweden

[21] Appl. No.: 835,958

[22] Filed: Mar. 4, 1986

[51] Int. Cl.$^4$ .................. G01N 35/08; G01N 1/18
[52] U.S. Cl. ........................... 436/179; 422/82; 436/53
[58] Field of Search .............. 436/47, 52, 53, 179; 422/81, 82

[56] References Cited

U.S. PATENT DOCUMENTS

| | | | |
|---|---|---|---|
| 3,615,234 | 10/1971 | Ludvigsen | 422/82 |
| 4,049,381 | 9/1977 | Burns et al. | 436/53 |
| 4,276,051 | 6/1981 | Ginsburg et al. | 422/64 |
| 4,512,953 | 4/1985 | Marsoner et al. | 436/53 |
| 4,536,369 | 8/1985 | Sakaruda et al. | 436/47 |
| 4,539,296 | 9/1985 | Manabe | 436/47 |

Primary Examiner—Michael S. Marcus
Attorney, Agent, or Firm—Davis Hoxie Faithful & Hapgood

[57] ABSTRACT

Automatic dilution apparatus and method are provided, and are operable in conjunction with automated sample liquid analysis systems to automatically dilute sample liquids as supplied thereby to automated sample liquid analysis apparatus. One embodiment of the dilution apparatus operates to dilute the sample liquids by flowing the sample liquids from the analysis system sample liquid supply conduit, diluting the same, and returning the diluted sample liquids to the supply conduit for flow therethrough to the sample analysis apparatus for sample liquid analysis. Flow of undiluted sample liquids through the supply conduit is prevented attendant operation of the dilution apparatus. A second embodiment of the dilution apparatus operates to remove predetermined volumes of the sample liquids from the supply conduit, and to replace the same with like volumes of a diluent liquid; thereby diluting the sample liquids in the supply conduit for continued flow to the sample liquid analysis apparatus. Both embodiments of the dilution apparatus are operable on demand; and the second apparatus embodiment is additionally operable to dilute the sample liquids to a varying degree throughout a predetermined dilution range.

20 Claims, 2 Drawing Sheets

DILUTION APPARATUS AND METHOD

BACKGROUND OF THE INVENTION

1. Field of The Invention

This invention relates to new and improved automated liquid dilution apparatus and method which are particularly adapted for use with automated sample liquid analysis systems.

2. Description of the Prior Art

U.S. Pat. No. 4,049,381 issued Sept. 20, 1977 to Donald A. Burns, Ph.D., et al, for Apparatus And Method of Fluid Sample Analysis, and assigned to the assignee hereof, discloses dilution apparatus and method directed to the preparation of concentration gradients in liquid samples; and, to this effect, comprises means for diluting a reagent liquid with an appropriate diluent liquid to a varying degree prior to the combination of the thusly diluted reagent liquid with a sample liquid. This dilution is achieved by withdrawing reagent liquid from a reagent liquid supply conduit at a varying flow rate, replacing the thusly withdrawn reagent liquid downstream in the supply conduit with a diluent liquid at substantially the same varying flow rate, and mixing the thusly variably diluted reagent liquid with a sample liquid for subsequent quantitative sample liquid analysis with regard to sample liquid constituent of interest.

The turbidometric assay system marketed by the Elanco Products Co., division of Eli Lilly Co., Indianapolis, Ind., under the Trademark "Autoturb" is designed to analyze the potency of antibiotics, vitamins and related substances; and, to this effect, includes a diluter module which functions to dilute sample liquids in sample liquid conduit lengths, or loops, of different volumes by introducing a selected one of those sample liquid volumes to a carrier stream which contains a fixed proportion of a diluent liquid. Thus, the extent to which the sample liquid is diluted by the diluent liquid in the carrier stream will be determined in accordance with the selected sample liquid volume which is introduced into the carrier stream. This system is described in Elanco's sales brochure entitled *AUTOTURB II*.

SUMMARY OF THE INVENTION

In a herein disclosed first embodiment of automated liquid dilution apparatus configured and operable in accordance with the teachings of our invention, the apparatus comprise dilution conduit means which connect to the sample liquid supply conduit means of automated sample liquid analysis system downstream of the system sampler. Dilution means are operatively connected to the dilution conduit means to dilute sample liquids fowing therein by the addition of a diluent liquid thereto. A second connection of the dilution conduit means to the supply conduit means is made downstream of the first such connection in the latter; and this connection comprises multiposition liquid flow control means, taking the form of a selector valve, which is operable in a first position thereof to connect the dilution conduit means to the sample liquid conduit means for the flow of the diluted sample liquids from the dilution conduit means back into the sample liquid supply conduit means for flow therethough to sample liquid analysis apparatus, while preventing the flow of undiluted sample liquids from the sampler through the sample liquid supply conduit means. In a second selector valve position, the same is operable to permit undiluted sample liquid flow from the sampler to the sample analysis apparatus through the sample liquid supply conduit means, while preventing the flow of the diluted sample liquids from the dilution conduit means back into the sample liquid supply conduit means. Utilization is made of the same sample liquid analysis pump to pump both the sample liquids and the diluent liquid in this invention embodiment.

In the herein disclosed second embodiment of automated liquid dilution apparatus configured and operable in accordance with the teachings of our invention, the apparatus comprise sample liquid removal conduit means which connect to the sample liquid supply conduit means of an automated sample liquid system downstream of the system sampler. Dilution conduit means connect to the sample liquid supply conduit means downstream in the latter of the sample liquid removal conduit means, and are operable to introduce a diluent liquid thereinto for dilution of said sample liquids. Further included in the dilution apparatus are independent pump means which are operatively connected to the sample liquid removal and dilution conduit means, and which are operable to concomitantly remove sample liquid from said sample liquid supply conduit means through said said liquid removal conduit means and replace the same with diluent liquid through said dilution conduit means, both at substantially the same flow rate. Variable speed pump drive means are provided to vary the flow rates of the sample and diluent liquids, respectively out of and into the sample liquid supply conduit means, thereby providing for the dilution of the sample liquids through predetermined dilution ranges. With the pump means retained stationary, no dilution of the sample liquids is accomplished.

In each instance, the automated liquid dilution apparatus of our invention may be readily added on to existing automated sample liquid analysis systems without complex and costly changes in the latter, and without requirement for change in the timing or other essential operational parameters of the analysis system.

Both of the apparatus embodiments are automatically operable on demand; with the first apparatus embodiment being automatically operable upon the simple positioning of the selector valve in the first position thereof, and the second apparatus embodiment being operable upon the simple commencement of the drive of the independent apparatus pump means.

OBJECTS OF THE INVENTION

It is, accordingly, an object of our invention to provide new and improved automated liquid dilution apparatus and method.

It is another object of our invention to provide apparatus and method as above which are particularly adapted for use with automated sample liquid analysis systems to dilute sample liquids attendant the automated analysis thereof.

It is another object of our invention to provide apparatus and method as above which are automatically operable on demand.

It is another object of our invention to provide apparatus and method as above which are of relatively simple and economical configuration and manner of operation.

It is another object of our invention to provide apparatus and method as above which may be readily and effectively added-on to existing automated sample liquid analysis systems without requirement for complex and costly change in those systems.

It is another object of our invention to provide apparatus and method as above which may be readily and effectively modified or controlled to provide for different liquid dilution factors.

It is another object of our invention to provide for apparatus and method as above which exhibit a very high degree of precision of operation.

It is another object of our invention to provide apparatus and method as above which can be operated to dilute successive liquids throughout the same varying dilution range.

It is a further object of our invention to provide apparatus as above which require the use of only readily available apparatus components of proven dependability in the fabrication thereof.

DESCRIPTION OF THE DRAWINGS

The above and other objects and significant advantages of our invention are believed made clear by the following detailed description thereof taken in conjunction with the accompanying drawings wherein.

DETAILED DESCRIPTION OF THE INVENTION

Figures 1, 1A:
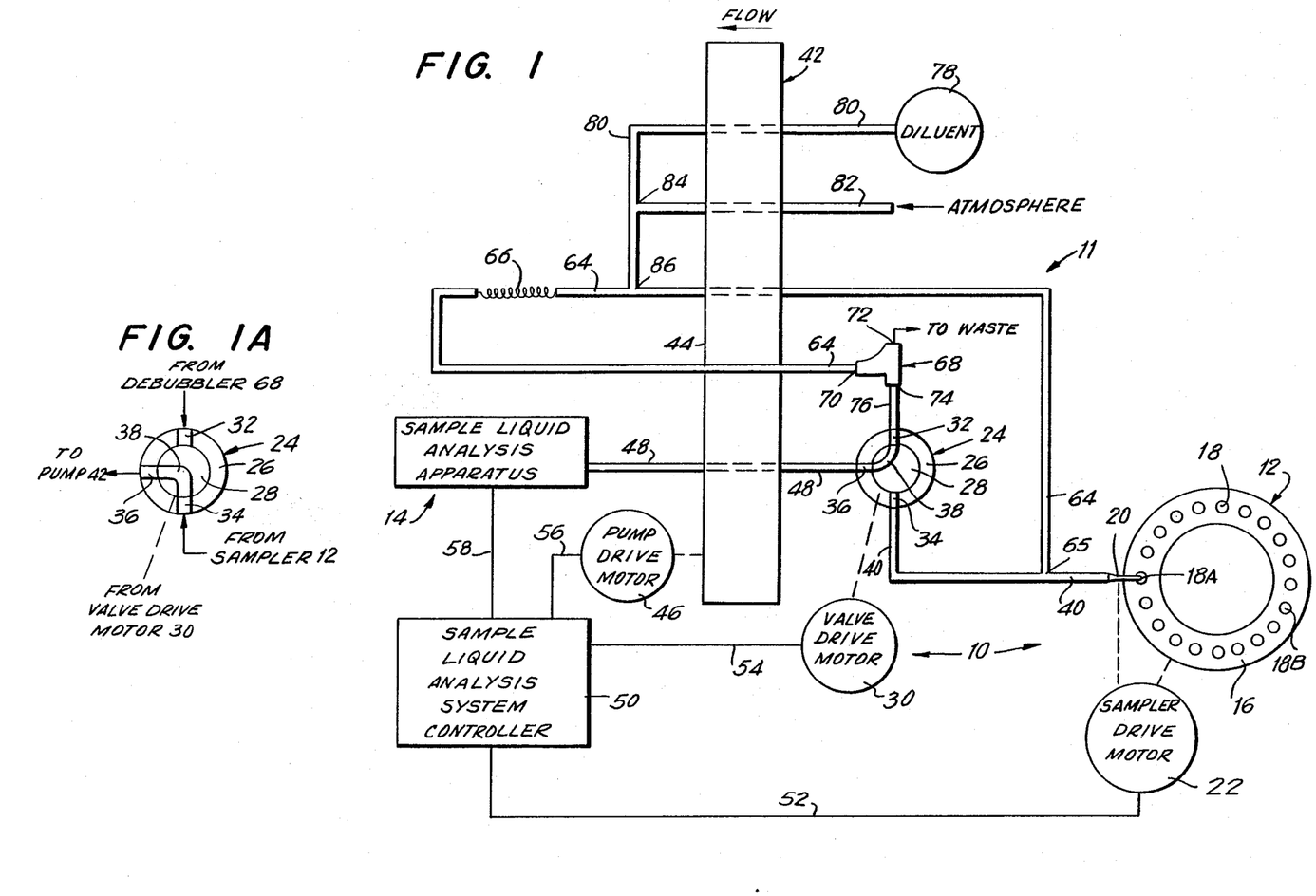
FIG. 1 is a schematic diagram of a first embodiment of new and improved automated liquid dilution apparatus representatively configured and operable in accordance with the teachings of our invention, and depicted in operative relationship with an automated sample liquid analysis system.
FIG. 1A is a schematic diagram of the selector valve of FIG. 1 depicted in a different operational condition thereof.

Referring now to FIGS. 1 and 1A of the application drawings, a representative automated sample liquid analysis system is schematically depicted as indicated generally at 10; and a first embodiment of automated sample liquid dilution apparatus representatively configured and operable in accordance with the teachings of our invention is schematically depicted as indicated generally at 11 in operable relationship with the analysis system 10.

The analysis system 10 comprises an automated sampler as indicated generally at 12, and automated sample liquid analysis apparatus as indicated generally at 14.

Sampler 12 is of conventional configuration and manner of operation; and, in manner well understood by those skilled in this art, comprises a turntable or like indexable device 16 upon which are supported as shown a plurality of spaced sample liquid containers 18 which respectively contain different sample liquids for analysis. A sample liquid aspiration probe is indicated at 20, and is operatively associated with turntable 16 to aspirate sample liquids from the containers 18 as the same are successively presented thereto attendant indexing of the turntable 16. A sampler drive motor is indicated at 22, and is mechanically connected as shown by the dashed lines to turntable 16 and aspirating probe 20 for synchronized operation thereof.

Sample liquid analysis apparatus 14 are also of conventional configuration and manner of operation; and, in manner well understood by those skilled in this art, are operable to automatically quantitatively analyze in turn sample liquids as successively presented thereto in the form of sample liquid stream with regard to the concentration(s) of one or more specified sample liquid constituents. Too this effect, analysis apparatus 14 may, for example, include non-illustrated sample liquid stream flow cell, and operatively associated light source and photo-detector.

A multi-port selector valve, which is common to both the analysis system 10 and the dilution apparatus 11, is indicated generally at 24; and comprises an outer valve body member 26 and an inner valve body member 28 movable relative thereto under the control of valve drive motor 30 which is mechanically connected thereto as shown by the dashed line. Outer valve body member 26 comprises spaced ports 32, 34 and 36; and inner valve body member 28 comprises a generally L-shaped flow passage 38. With the inner valve body member 28 moved by drive motor 30 to the FIG. 1 position thereof, flow passage 38 operates to connect valve ports 32 and 36; while with the body member 28 moved to the FIG. 1A position thereof, flow passage 38 operates to connect valve ports 34 and 36.

A flexible principal sample liquid conduit of any appropriately sturdy and chemically inert material, for example polyvinylchloride tubing of standard laboratory specification, is indicated at 40 and extends as shown to connect aspirating probe 20 to port 34 of the selector valve 24.

A conventional peristaltic or compressible tube pump, which is also common to the analysis system 10 and the dilution apparatus 11, is indicated generally at 42; and, in manner well understood by those skilled in this art, comprises a pump platen as indicated at 44, and a plurality of spaced pump rollers, not shown, which are operatively associated with the platen and drivable in the direction from right to left as seen in FIG. 1 to progressively occlude one or more flexible pump tubes against the platen to pump liquid(s) therethrough in the indicated direction.

An electric pump drive motor is indicated at 46 and is mechanically connected as shown by the dashed line to pump 44 to drive the same.

A flexible downstream conduit is indicated at 48; and extends as shown to connect selector valve port 36 to the sample liquid analysis apparatus 14. Conduit 48 operatively extends as illustrated through the compressible tube pump 42 to form one of the compressible pump tubes.

A sample liquid analysis system controller, taking for example the by now conventional form of an appropriately programmable microprocessor device, is indicated generally at 50; and is electrically connected as shown by lines 52, 54, 56 and 58 to each of sampler drive motor 22, selector valve drive motor 30, pump drive motor 46, and sample liquid analysis apparatus 14, to control and synchronize the respective operations thereof.

With the sample liquid analysis system 10 configured and operable as described, and with selector valve 24 rotated to the FIG. 1A position thereof by valve drive motor 30 to connect conduit 40 to conduit 48 therethrough, it will be readily understood by those skilled in this art that the thusly interconnected sampler 12, pump 42 and analysis apparatus 14 will function to provide an essentially conventional, single channel automated sample liquid analysis system; with undiluted sample liquids being provided in turn in the form of a continuous sample liquid stream from sampler 12 through pump 42 to analysis apparatus 14 for sequential automated sample liquid analysis. Of course, additional sample liquid processing and/or treatment components, for example mixing or incubation coils, de-bubbler devices, or reagent source(s) and appropriate conduit(s) to combine the sample liquid stream with an appropriate reagent(s) stream, none of which is illustrated, may be included in conventional manner in the sample liquid analysis system 10 as may be required by the particular nature of the sample liquids under automated analysis, and/or the particular sample liquid constituent(s) of interest. Automated sample liquid analysis systems of this nature are by now well known and understood in this art; and one such system is disclosed in U.S. Pat. No. 3,241,432 issued Mar. 22, 1966 to Leonard T. Skeggs, Ph.D., et al, and now expired, the disclosure of which is hereby incorporated herein.

The automated sample liquid dilution apparatus 11, which are representatively configured and operable in accordance with the teachings of first embodiment of our invention to provide for the automatic dilution on demand of selected ones of the sample liquids from sampler 12, comprise flexible auxiliary sample liquid conduit 64 which extends as shown from a juncture 65 with principal sample liquid conduit 40 intermediate aspirating probe 20 and selector valve 24 to extend operatively through pump 42 to thereby form another of the compressible pump tubes. A mixing coil is indicated at 66, and is connected as shown in conduit 64 downstream of pump 42. A conventional de-bubbler fitting is indicated generally at 68, and is operable in manner well understood by those skilled in this art to remove air segments, or "bubbles" from air-segmented sample liquid stream upon the flow of the same therethrough. To this effect, de-bubbler fitting 68 comprises an inlet 70 for the segmented sample liquid stream, an outlet 72 for the flow of the removed air segments to waste, and an outlet 74 for the flow of the "de-bubbled" sample liquid stream from the fitting. Conduit 64 extends as shown, without further operable connection with pump 42, to connect the outlet of mixing coil 66 to the inlet 70 of the de-bubbler fitting 68; and a flexible conduit 76 extends as shown to connect de-bubbler fitting outlet 74 to selector valve port 32.

A source of an appropriate sample liquid diluent, for example distilled water, is indicated at 78; and a flexible dilution liquid conduit 80 extends therefrom as shown operatively through pump 42 to form another of the compressible pump tubes.

A flexble conduit 82, with the inlet end thereof open to atmosphere as indicated on FIG. 1, operatively extends as shown through pump 42 to form the fourth and final compressible pump tube. Conduit 82 joins as shown with conduit 80 as indicated at 84; and conduit 80 joins in turn as shown with conduit 64 as indicated at 86 downstream of the juncture 84 thereof with conduit 82.

With the automated sample liquid analysis system configured and operable as described and in use, for example, for the successive automated analyses of a plurality of environmental sample liquids such as well water samples or the like to determine the concentration levels of a specified pollutant therein throughout a reasonable predetermined concentration level range, it will be readily understood by those skilled in this art that, on occasion, the concentration level of the pollutant of interest in one or more of the sample liquids under analysis will be so high as to simply drive the sample liquid analysis apparatus off the high end of the included concentration level recording scale. Thus, the requisite capability of accurately quantifying this particular concentration level is lost to the analysis apparatus.

In accordance with the teachings of our invention, this problem is readily and effectively overcome as follows. With system controller 50 appropriately programmed, it will be clear that at the end of a sample liquid run, turntable 16 and aspiration probe 20 can be automatically instructed by controller 50 to re-run, by re-sampling in turn, each of the sample liquids which resulted in an off-scale pollutant concentration level; while the analysis apparatus 14 can be likewise instructed by controller 50 to operate in a higher concentration level mode. The sample liquids with the unduly high pollutant concentration levels may, for example, be constituted by the sample liquids in the turntable containers as indicated at 18A and 18B in FIG. 1. Concomitantly, controller 50 would instruct valve drive motor 30 to rotate selector valve 24 to the FIG. 1 position thereof to connect valve ports 32 and 36; thereby effectively placing the dilution apparatus 11 of our invention on-line with the analysis system 10, and sealing off selector valve port 34.

With the dilution apparatus 11 placed on-line as described, and sample liquid container 18A returned to the operable position thereof as shown in FIG. 1 relative to the aspiration probe 20, it will be clear that the sample liquid from the container 18A will be pumped by pump 42 through conduits 40 and 64; while sample liquid flow in the portion of conduit 40 downstream of the juncture 65 with conduit 64 will be prevented by the closed selector valve port 34.

Concomitantly, a synchronized stream of an air-segmented diluent will be supplied by pump 42 through conduits 80 and 82 to merge with the sample liquid stream in conduit 64 at conduit juncture 86 for flow therewith through mixing coil 66. As a result, a thoroughly mixed, air-segmented diluted sample liquid stream of the sample liquid from turntable container 18A will be flowed to de-bubbler fitting 68 for removal of the air segments therefrom; and flow from fitting 68 through conduit 76 and selector valve 24 for pumping via conduit 48 to the sample analysis apparatus 14 and analysis on an appropriately higher pollutant concentration level scale to precisely quantify the concentration level of interest. Aspiration by probe 20 of the sample liquid from container 18A as described is immediately followed by instructions from controller 50 to index turntable 16 to present sample liquid container 18B to the aspiration probe 20 for a repeat of the steps described with regard to the aspiration, automated dilution and analysis of the sample liquid from container 18B.

With the components of the automated dilution apparatus 11 of our invention now described in detail, and referring again to operation of the sample liquid analysis system 10 with selector valve 24 in the FIG. 1A position to supply undiluted sample liquids to analysis apparatus 14, it will be clear that the sample liquids supplied to conduit 40 from aspiration probe 20 will be divided at conduit juncture 65, with sample liquid flowing in conduit 64 to the dilution apparatus 11 as well as directly to and through selector valve 24 as described. Thus, even with selector valve 24 in the FIG. 1A position thereof, the dilution apparatus 11 will function essentially as described with regard to the provision of an air-segmented, diluted sample liquid stream to the inlet 70 of the de-bubbler fitting 78. However, and since under this operational condition, port 32 of the selector valve 24 is closed, this entire air-segmented, diluted sample liquid stream will simply be forced to flow to waste as indicated through de-bubbler fitting outlet 72.

The dilution factor, e.g. the extent to which the re-run sample liquids are automatically diluted by the apparatus of our invention with selector valve 24 in the FIG. 1 position thereof, is readily determined and controlled by proper selection of the internal diameters, and thus of the internal cross-sectional areas, of the conduits 64 and 80 which each form a compressible pump tube as described. For example, if the internal diameter, and thus internal cross-sectional area, of conduit 64 is selected, in accordance with the other controlling operational parameters of the compressible tube pump 42 and the analysis system 10 as a whole, to aspirate and pump sample liquids from sampler 12 at 0.2 mL/min., and the internal diameter, and thus internal cross-sectional area, of conduit 80 selected as above to pump diluent from diluent source 78 at 1.8 mL/min., the total liquid flow supplied to analysis apparatus 14 will, of course, be 2.0 mL/min., of which only 10% will be sample liquid. Thus, a dilution factor of precisely 10 is provided; and it will be clear to those skilled in this art that this dilution factor may be readily and effectively changed, within a very wide range of realistic dilution factors and without any sacrifice in dilution factor precision, by simple change is the internal diameter, and thus internal cross-sectional area, of conduit 80.

Regarding consistency of sample liquid analysis system timing under both undiluted and diluted sample liquid supply and analysis conditions as described, it will be clear that fluid flow—both sample liquid and air—from conduits 64, 80 and 82 through mixing coil 66 with the selector valve 24 in the FIG. 1 position thereof to provide diluted sample liquids for analysis, will always be significantly faster than sample liquid flow through conduit 40 with the selector valve 24 in the FIG. 1A position to provide undiluted sample liquids of analysis. Since this faster flow rate is in conduit 64 which is necessarily considerably longer than conduit 40, and which further includes de-bubbler fitting 68 upstream of selector valve 24, it is clear that appropriate selection of the overall lengths of conduits 64 and 76, relative to the length of conduit 40, will function to insure that undiluted and diluted sample liquids arrive at selector valve 24 at precisely the same time interval after aspiration thereof by probe 20. Thus, no adjustment in the essential timing of analysis system 10 is required when one or more sample liquids must be re-run as described for dilution and repeat analysis.

The above makes clear that the dilution apparatus 11 of our invention may be readily added on to existing automated sample liquid analysis systems of the type described without complex and costly change in the latter, through the simple connection of selector valve 24 in conduits 40 and 48 to connect conduit 76 thereto, and control flow through said conduits, the simple connection of conduits 64 and 40 by conduit connecting means, for example a standard laboratory "T" fitting of appropriate internal diameters, and the operable extension of conduits 64, 82 and 80 through system pump 42 to form compressible pump tubes.

Figure 2:
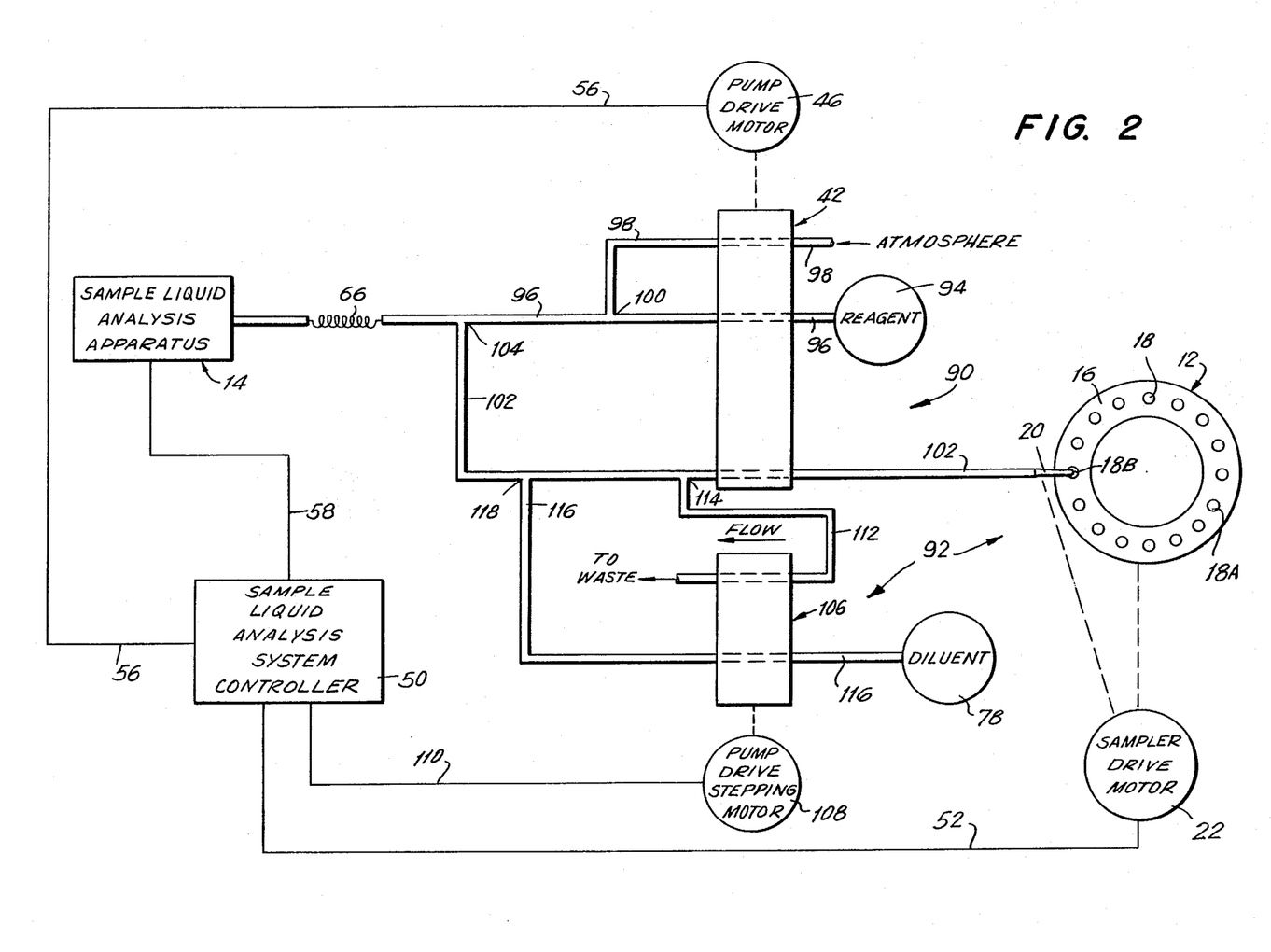
FIG. 2 is a schematic diagram of a second embodiment of new and improved automated liquid dilution apparatus representatively configured and operable in accordance with the teachings of our invention, and depicted in operative relationship with an automated sample liquid analysis system.

Referring now to FIG. 2 of the application drawings, another representative automated sample liquid analysis system is schematically depicted as indicated generally at 90; and a second embodiment of automated sample liquid dilution apparatus representatively configured and operable in accordance with the teachings of our invention is schematically depicted as indicated generally at 92 in operable relationship with the analysis system 90. Like analysis system and dilution apparatus components bear the same identifying numerals in FIG. 2 as utilized therefor in FIG. 1.

The sample liquid analysis system 90 of FIG. 2 is again of conventional configuration and manner of operation; and, to this effect, again includes a sampler 12, compressible tube pump 42, sample liquid analysis apparatus 14, sampler drive motor 22, pump drive motor 46, and system controller 50, all configured and operable as described hereinabove with regard to sample liquid analysis system 10 of FIG. 1. Sample liquid analysis system 90 additionally comprises a source 94 of an appropriate sample liquid reagent, for example color-producing; and a flexible conduit 96 extends operatively therefrom through pump 42 to form a compressible pump tube which connects as shown to the analysis apparatus 14. Flexible conduit 98, having one end thereof open to atmosphere, operatively extends through pump 42 to form another compressible pump tube, and thereafter joins as shown with conduit 96 as indicated at 100. Flexible conduit 102 is operatively connected to the aspiration probe 20, and operatively extends through pump 42 to form another compressible pump tube. Conduit 102 then joins as shown with conduit 96 as indicated at 104 downstream of conduit juncture 100. Mixing coil as again indicated at 66 is connected as shown in conduit 96 downstream of conduit juncture 104.

The sample liquid dilution apparatus 92 of our invention comprise an independent compressible tube pump as generally indicated at 106 which is driven as shown by an electric stepping, or variable speed, pump drive motor 108. Pump drive motor 108 is in turn electrically controlled as indicated along line 110 from system controller 50. A flexible conduit 112 joins as shown with analysis system conduit 102 as indicated at 114 downstream of system pump 42, and operatively extends therefrom as shown through dilution apparatus pump 10 to form a compressible pump tube, and therefrom to waste as indicated. A flexible conduit 116 operatively extends from diluent source 78 as shown through pump 106 to form the second and final compressible tube of that pump; and extends as shown from the latter to join conduit 102 as indicated at 118 downstream of the juncture 114 of conduit 112 with conduit 102.

With the automated sample liquid analysis system 90, and the automated dilution apparatus 92 of our invention configured as depicted in FIG. 2, and with pump drive motor 108, and accordingly pump 106, retained stationary on instructions from system controller 50, it will be clear to those skilled in this art that synchronized operation of sampler 12, pump 42 and sample liquid analysis apparatus 14 on instruction from controller 50 will result in the supply of an air segmented stream of successive, appropriately mixed and reacted sample liquids from the sample containers 18 to the analysis apparatus 14 for successive sample liquid analyses as described; it being equally clear that the occlusion of flexible conduits 112 and 116 by the stationary, non-illustrated pump rollers of compressible tube pump 106 will prevent sample liquid flow into conduits 112 and 116 from conduit 102 beyond pump 106, and will prevent diluent flow from source 78 into the sample liquid stream in conduit 102.

For operation of the dilution apparatus 92 to provide a single predetermined dilution factor for selected ones, only, of the sample liquids, again for example those from turntable containers 18A and 18B in the face of off-scale high sample liquid constituent concentration level readings, the sample liquids from containers 18A and 18B would again be automatically re-run under instructions from controller 50 to sampler 12 as described in detail hereinabove with regard to the sample liquid analysis system 10 of FIG. 1. Concomitantly, pump drive motor 108 would be instructed by controller 50 to operate at a constant speed predetermined to provide the predetermined dilution factor for the sample liquids of interest. More specifically, and to provide a dilution factor of 5, dilution apparatus pump 106 would be driven at a speed predetermined in accordance with the relationship between the respective internal diameters of conduits 112 and 116, which are of course the same, and the internal diameter of conduit 102 and the speed of operation of analysis system pump 42, to withdraw 80% of the sample liquid stream from conduit 102 through conduit 112 for pumping to waste, and replacing the same with a like amount of diluent from source 78 through conduit 116. Since, in this embodiment of the dilution apparatus of our invention, the dilution factor is controlled solely by the speed of pump 106, which may of course range from zero to result in no sample liquid dilution or a dilution factor of 1, to a sufficiently high speed to result in the removal of all of the sample liquid stream in conduit 102 through conduit 112 and the replacement thereof with a like quantity of diluent through conduit 116 to thereby result in infinite sample liquid "dilution," it is clear that the dilution apparatus may be readily operated to provide any desired sample liquid dilution factor.

As an alternative to the above, it is clear that the dilution apparatus 92 of our invention may, by virtue of appropriate change in the speed of pump drive motor 108, and thus in the sample liquid and diluent flow rates through pump conduits 112 and 116, throughout a predetermined range attendant the flow of the sample liquid from each of the turntable containers 18, provide for the dilution of each of said sample liquids in turn throughout the same predetermined dilution range. Thus, every sample liquid could be run at may dilutions; thereby providing, for each of the sample liquids a sample constituent concentration gradient via a ramp function to thereby enable comprehensive sample liquid analysis of each sample liquid with but a single run of the same through the analysis apparatus 14. This speed, and thus pump flow rate, change could, in accordance with appropriate programming of analysis system controller, be linear, logarithmic, exponential, or in accordance with any other mathematically definable function; and this capability of the dilution apparatus 92 of FIG. 2 could prove of particular utility, for example, in the automated analyses of a plurality of human blood samples with regard to constituent(s) of interest thereof.

Regarding essential consistency of timing of the automated sample liquid analysis system 90 under both diluted and undiluted sample liquid supply and analysis conditions as described, it is clear that, since both diluted and undiluted sample liquids from sampler 12 will arrive at conduit juncture 104 at exactly the same time interval after the sampling thereof, no adjustment in the operational timing of sample liquid analysis system 90 will be required by the addition of the dilution apparatus 92 thereto.

Again, the dilution apparatus 92 of our invention may be readily added on to existing automated sample liquid analysis systems of the type described without complex and costly change in the latter; in this instance by the simple connection of conduits 112 and 114 through use of appropriate conduit connecting means, and the additional connection of control line 110 to the sample liquid analysis system controller 50 to control pump drive motor 108.

Of course, and with regard to both automated dilution apparatus 11 and automated dilution apparatus 92 of our invention, it is clear that appropriate re-programming of the sample liquid analysis system controller 50 would be required in all instances wherein the dilution apparatus were added on as described to an existing sample liquid analysis system.

Although, for consistency and convenience of description, all analysis system and dilution apparatus conduits have been described as "flexible," it will be clear to those skilled in this art that only those portions thereof which extend through the compressible tube pumps to form compressible pump tubes as described must, of necessity, be flexible; and that the remaining portions of the conduits could readily be inflexible and made, for example, from standard laboratory tubing of appropriate internal daimeter(s).

Regarding segmentation as described of the diluent liquid stream in conduit 80 of the dilution apparatus 11 of FIG. 1, it will be clear that the segmenting fluid is not restricted to air, but rather, could be constituted by a different gas, or by a suitable liquid which is immiscible with the sample liquids. In such instances, the different gas, or liquid, would be supplied to the inlet end of conduit 82 from appropriate sources thereof, not shown. For use of the dilution apparatus 11 with an immiscible diluent liquid, de-bubbler fitting 68 would be replaced by suitable phase separator means, not shown, in manner well understood by those skilled in this art.

Various changes may, of course, be made in the herein-disclosed embodiments of our invention without departing from the spirit and scope thereof as defined by the appended claims.

What is claimed is:

1. A method for diluting sample liquids for chemical analsis comprising the steps of;
    flowing said sample liquid through a principal sample liquid conduit means;
    dividing the flow of said sample liquid at a first junction means;
    flowing a portion of said divided sample liquid through an auxiliary sample liquid conduit means connected to said first junction means;
    adding a dilution liquid to said sample liquid flowing in said auxiliary sample liquid conduit means at a second junction means such that diluted sample liquid flows in said auxiliary sample liquid conduit means;
    continuing the flow of said sample liquids in said principal sample liquid conduit means through a conduit connection means to a downstream conduit means and preventing the flow of diluted sample liquids from said auxiliary sample liquid conduit means to said downstream conduit means at said conduit connection means such that liquid flow in said downstream conduit means will be restricted to said sample liquids.

2. The method claimed in claim 1, further comprising; preventing the flow of said sample liquids from said principal sample liquid conduit means to said downstream conduit means at said conduit connection means and allowing the flow of said diluted sample liquids from said auxiliary sample liquid conduit means through said conduit connection means to said downstream conduit means such that liquid flow in said downstream conduit means will be restricted to said diluted sample liquids.

3. The method as claimed in claim 2, wherein said steps of flowing of said sample liquids and said adding of said diluted sample liquids comprises the pumping of said liquids.

4. The method as claimed in claim 2, further comprising the steps of, continuing the flow of said diluted sample liquids in said auxiliary sample liquid conduit means concomitantly with the flow of said sample liquids through said conduit connection means from said principal sample liquid conduit means.

5. The method as claimed in claim 2, further comprising the steps of, adding a segmenting fluid to said diluted sample liquids in said auxiliary sample liquid conduit means to segment said sample liquids, and mixing said segmented diluted sample liquids in said auxilary sample liquid conduit means.

6. The method as claimed in claim 5, further comprising the steps of, removing said segmenting fluid from said segmented diluted sample liquids in said auxiliary sample liquid conduit means prior to the flow thereof through said conduit connection means into said downstream conduit means.

7. An automatic sample liquid dilution apparatus for diluting sample liquids for chemical analysis, said apparatus comprising;
principal sample liquid conduit means for conveying sample liquid;
auxiliary sample liquid conduit means and first junction means connecting said auxiliary sample liquid conduit means to said principal sample conduit means such that sample liquids can concurrently flow in said auxiliary sample liquid conduit means;
dilution liquid supply means and dilution liquid conduit means for conveying dilution liquid from said dilution liquid supply means;
second juncton means connecting said dilution conduit means to said auxiliary sample liquid conduit means for diluting said sample liquids flowing in said auxiliary sample liquid conduit means;
downstream conduit means for conveying either sample liquid from said principal sample liquid conduit means or diluted sample liquid from said auxiliary sample liquid conduit means downstream of said dilution apparatus;
conduit connection means connecting said principal sample liquid conduit means and said auxiliary sample liquid conduit means to said downstream conduit means, said conduit connection means being downstream of said first and second junction means;
said conduit connection means comprising automatic multi-position flow control means having a first position for allowing the flow of sample liquid from said principal sample liquid conduit means to said downstream conduit means and preventing the flow of diluted sample liquid from said auxiliary sample liquid conduit means, and a second position for preventing the flow of sample liquids from said principal sample liquid conduit means to said downstream conduit means and allowing the flow of diluted sample liquid from said auxiliary sample liquid conduit means to said downstream conduit means, said multi-position flow control means being automatically switched between said first and second positons; and
pump means for pumping said sample liquid, said dilution liquid and said diluted sample liquid through each of said conduit means.

8. The sample liquid dilution apparatus claimed in claim 7, wherein said multi-position flow control means comprises valve means operatively connecting said principal sample liquid conduit means and said auxiliary sample liquid conduit means to said downstream conduit means, said valve means being operable in said first position to open said downstream conduit means to the flow of sample liquids and to close said downstream conduit means to the flow of diluted sample liquids, said valve means being operable in said second position to close said downstream conduit means to the flow of sample liquids and open said downstream conduit means to the flow of diluted sample liquids.

9. The sample liquid dilution apparatus as claimed in claim 7, wherein said pump means are operatively connected to said auxiliary sample liquid conduit means, said dilution conduit means and said downstream conduit means.

10. The sample liquid dilution apparatus as claimed in claim 9, wherein said pump means are formed by the same pump.

11. The sample liquid dilution apparatus as claimed in claim 10, wherein said pump comprises a compressible tube pump and said auxiliary sample liquid conduit means and said dilution means comprise compressible tubes of said pump whereby, the extent to which said sample liquids are diluted by said dilution liquid in said auxiliary sample liquid supply conduit means may be determined in accordance with the ratio between the cross-sectional areas of the compressible pump tubes which are included in said auxiliary sample liquid supply means and said dilution conduit means.

12. The sample liquid dilution apparatus as claimed in claim 11, wherein said downstream conduit means also comprises a compressible tube of said pump.

13. The sample liquid dilution apparatus as claimed in claim 8, further comprising, segmenting fluid adding means operatively associated with said auxiliary sample liquid conduit means for adding a segmenting fluid to said diluted sample liquids in said auxiliary ample liquid conduit means to segment said diluted sample liquids, and mixing means in said auxiliary sample liquid conduit means downstream of said segmenting fluid adding means to mix the segmented diluted sample liquids.

14. The sample liquid dilution apparatus as claimed in claim 13, further comprising, means insaid auxiliary sample liquid conduit means upstream of said conduit connecting means for permitting continued flow of said diluted sample liquids in said auxiliary sample liquid conduit means when said multi-position flow control means are in said first position.

15. The sample liquid dilution apparatus as claimed in claim 13, further comprising, means in said auxiliary sample liquid conduit means downstream of said mixing means for removing said segmenting fluid from said segmented diluted sample liquids.

16. An automatic sample liquid dilution apparatus for use in selectively diluting samples for chemical analysis, said apparatus comprising;

principal sample conduit means for conveying sample liquids, auxiliary sample liquid conduit means and a first T-fitting connecting said auxiliary liquid sample conduit means to said principal sample liquid conduit means such that sample liquid flows through said auxiliary sample liquid conduit means;

dilution liquid supply means and a dilution liquid conduit means connected to said dilution liquid supply means;

a second T-fitting connecting said dilution liquid conduit means to said auxiliary sample liquid conduit means for introducing dilution liquid into said auxiliary sample liquid conduit means for diluting said sample liquid;

downstream conduit means, and a conduit connecting means downstream of said first and second T-fittings, selectively connecting either said principal sample liquid conduit means or said auxiliary sample liquid conduit means to said downstream conduit means, such that either sample liquid or diluted sample liquid can flow through said downstream conduit means;

said conduit connecting means comprising an automatic valve means having a first position allowing sample liquid in said principal sample liquid conduit means to flow into said downstream conduit means and blocking said auxiliary sample liquid conduit means, and a second position allowing said diluted sample liquid in said auxiliary sample liquid conduit means to flow into said downstream conduit means and blocking said principal sample liquid conduit means, said connecting means capable of being automatically switched between said first and second positions;

said auxiliary sample conduit means comprising a waste flow means allowing said diluted sample liquid to flow to waste when said valve means is in its first position such that said diluted sample liquid can continuously flow; and pump means for pumping said sample liquid, said dilution liquid and said diluted sample liquid through each of said conduit means.

17. An automatic sample liquid dilution apparatus as claimed in claim 16, wherein said waste flow means allows excess diluted sample liquid to flow to waste when said multi-position flow control means is in its second position.

18. An automatic sample liquid dilution apparatus as claimed in claim 16, wherein said pump means are formed by the same pump.

19. An automatic sample liquid dilution apparatus as claimed in claim 17, further comprising segmenting fluid adding means associated with said auxiliary sample liquid conduit means for adding a segmenting fluid to said diluted sample liquid in said auxiliary sample liquid conduit means to segment said diluted sample liquid, and mixing mens in said auxiliary sample liquid conduit means downstream of said segmenting fluid adding means to mix said segmented diluted sample liquids.

20. A dilution apparatus as in claim 19 further comprising means in said auxiliary sample liquid conduit means downstream of said mixing means for removing said segmenting fluid from said segmented diluted sample liquids.

* * * * *

UNITED STATES PATENT AND TRADEMARK OFFICE
CERTIFICATE OF CORRECTION

PATENT NO. : 4,826,775
DATED : May 2, 1989
INVENTOR(S) : Burns, Donald A.; Buccafuri, Anthony F.

It is certified that error appears in the above—identified patent and that said Letters Patent is hereby corrected as shown below:

Col. 1, line 53, replace "fowing" with "flowing".

Col. 7, line 4, replace "78" by "68".

Col. 7, line 32 replace "is" with "in".

Col. 8, line 47, replace "10" by "106".

Claim 1, line 2, replace "analsis" with "analysis".

Claim 7, line 14, replace "junton" with "junction".

Claim 14, line 2, replace "insaid" with "in said".

Claim 19, line 7, replace "mens" with "means".

Signed and Sealed this

Twelfth Day of March, 1991

Attest:

HARRY F. MANBECK, JR.

Attesting Officer

Commissioner of Patents and Trademarks